United States Patent [19]

Helzel et al.

[11] Patent Number: 4,664,129
[45] Date of Patent: May 12, 1987

[54] OPTICAL MOVEMENT SENSOR

[75] Inventors: Thomas Helzel, Hamburg; Jürgen Kordts, Wedel; Gerhard Martens, Ellerau, all of Fed. Rep. of Germany

[73] Assignee: U.S. Philips Corporation, New York, N.Y.

[21] Appl. No.: 849,917

[22] Filed: Apr. 9, 1986

[30] Foreign Application Priority Data

Apr. 15, 1985 [DE] Fed. Rep. of Germany ....... 3513400

[51] Int. Cl.$^4$ .............................................. A61B 5/10
[52] U.S. Cl. ................................. 128/774; 128/782; 128/721
[58] Field of Search ....................... 128/721, 774, 782; 73/800; 250/215, 224; 356/32

[56] References Cited

U.S. PATENT DOCUMENTS

| 3,268,845 | 8/1966 | Whitmore | 128/721 |
| 3,462,223 | 8/1969 | Tiemann et al. | 73/800 |
| 3,517,999 | 6/1970 | Weaver | 128/721 |
| 3,782,368 | 1/1974 | Rebold | 128/721 |
| 4,010,632 | 3/1977 | Sleringer et al. | 73/800 |
| 4,321,831 | 3/1982 | Tomlinson et al. | 73/800 |
| 4,342,907 | 8/1982 | Macedo et al. | 73/800 |
| 4,420,251 | 12/1983 | James et al. | 73/800 |
| 4,451,730 | 5/1984 | Brogardh et al. | 356/32 |
| 4,559,953 | 12/1985 | Wright et al. | 128/680 |

FOREIGN PATENT DOCUMENTS

| 2456314 | 1/1981 | France | 128/782 |
| 8404439 | 11/1984 | World Int. Prop. O. | |
| 0929058 | 5/1982 | U.S.S.R. | 128/774 |

OTHER PUBLICATIONS

"Respiration Transducer", Willis, IBM Technical Disclosure Bulletin, Nov. 1963.

Primary Examiner—Kyle L. Howell
Assistant Examiner—Max F. Hindenburg
Attorney, Agent, or Firm—Marc D. Schechter

[57] ABSTRACT

An optical movement sensor for clearly accurately detecting deformations of a human body. The movement sensor consists of a belt with a buckle made up of two parts which are joined together mechanically by a light-transmitting sensor element. Transmitting and a receiving fibre optic light guides are connected to one part of the buckle in such a way that light emitted by the transmitting light guide passes through the sensor element by way of a polarizer and is coupled to the receiving light guide via an analyzer.

8 Claims, 4 Drawing Figures

OPTICAL MOVEMENT SENSOR

BACKGROUND OF THE INVENTION

The invention relates to an optical movement sensor for the detection of a human body.

In computerized tomography, particularly nuclear spin tomography, intestinal, swallowing and muscular movements of a human body as well as movements originating from respiratory or heart activities produce so-called artefacts (i.e. shadows on the images of cross-sections lying at right angles to the body axis). The artefacts can falsify the examination result. To obtain perfect sectional images it is necessary therefore to clearly detect deformations of a human body under examination and take these into account in the production of the sectional images.

German Pat. No. 8012386 (corresponding to U.S. Pat. No. 4,559,953) describes a capsule-shaped sensor for the detection of deformations of a human body. The sensor contains a hollow space sealed off with an elastic membrane and filled with air. The hollow space has an aperture which is connected via a hose to a volume transducer.

The sensor is fixed by adhesive strips to the human body under examination in such a way that the elastic membrane lies on the body and is deflected with deformations of the body. The change which this brings about in the volume of the hollow space is detected and indicated by the volume transducer.

Because the membrane has a very thin wall, air in the sensor is heated up. The heated air expands causing the measured results supplied by the volume transducer to exhibit a measuring error which depends the temperature of the capsule-shaped sensor. Thus, the measured results depend on both the shape of the body being examined and on the temperature of the sensor. The measured results cannot therefore unequivocally indicate the state of deformation of the body.

SUMMARY OF THE INVENTION

It is an object of the invention to create an optical movement sensor which unequivocally indicates independent of the body temperature, the state of deformation of the human body under examination at particular points in time.

This object is achieved in an optical movement sensor of the type described above by a belt to be placed around the body of a patient. The belt comprises a buckle made up of two parts which are mechanically connected to one another by way of a light-transmitting sensor element. In one part of the buckle transmitting and receiving fiber optic light guides are connected to the sensor element by way of a polarizer or analyzer in such a way that light emitted by the transmitting light guide passes through the sensor element by way of the polarizer and then arrives in the receiving light guide by way of the analyzer.

If the human body undergoes deformation, the stress on the belt and therefore on the light-transmitting sensor element changes. As a result, the state of polarization of polarized light is changed when it passes through the sensor element. An analyzer filters out plane-polarized light from the polarized beam. The intensity of the filtered light varies with the state of polarization of the light, and thus unequivocally provides and largely temperature-independent information on the stress state of the belt and, therefore, on the state of deformation of the body.

A sensor which is simple and inexpensive to make is obtained if the receiving light guide is mounted on the opposite side of the sensor element to the transmitting light guide.

To increase the sensitivity of the movement sensor it is advantageous if the transmitting and receiving light guides are mounted on the same side of the sensor element and a mirror is mounted on the opposite side of the sensor element to the light guides. The mirror reflects the light which is emitted by the transmitting light guide and which passes through the sensor element back through the sensor element and passes it onto the receiving light guide. In this way, the light passes through the sensor element twice so that the polarization of the light is altered twice in the same direction as a function of the stress on the movement sensor.

In one advantageous configuration of the movement sensor, one buckle part has a socket for a fiber optical plug. The socket is connected to the transmitting and receiving light guides. Between the ends of the light guides and the sensor element, the socket contains a polarization foil which functions as a polarizer for the light emitted from the transmitting light guide. The foil functions as an analyzer for the light which is passed from the mirror to the receiving light guide. In this case, only a single fiber optical plug is required to connect the transmitting and receiving light guides to the movement sensor. Furthermore, the two light guides can be accommodated in one fiber optical cable so that the patient is not so inconvenienced by individual light guides.

In order to avoid measuring errors in nuclear spin tomography as the result of magnetic fields caused by eddy currents in electrically conductive parts of the movement sensor, it is essential that the optical movement sensor be made from nonmetallic materials.

DESCRIPTION OF THE PREFERRED EMBODIMENTS

Figure 1:
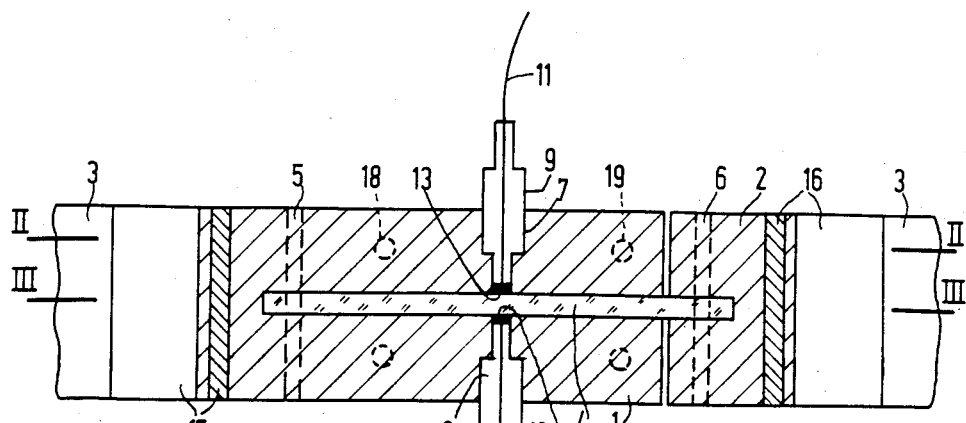
FIG. 1 is a cross-sectional view of the two-part buckle along the line I—I in FIGS. 2 and 3.

FIG. 1 is a sectional view of the buckle consisting of buckle parts 1 and 2. The two parts 1 and 2 of the buckle are each mechanically connected to one end of a belt 3. Belt 3 is placed around the upper body or stomach of a patient undergoing examination. In addition, the two parts 1 and 2 of the buckle are mechanically connected to one another by way of a light-transmitting sensor element 4 in the form of an oblong plate. In this case the sensor element 4 is fixed to buckle parts 1 and 2 by cotter pins 5 and 6.

One buckle part 1 has a socket 7 on one side and a socket 8 on the other side of the sensor element. Into these sockets 7 and 8 can be inserted fiber optical plugs 9 and 10 for transmitting and receiving light guides 11 and 12, respectively. The fiber optical plugs 9 and 10 each contain, between the ends of the transmitting and receiving light guides 11 and 12 and the sensor element 4, an polarization foil 13 and 14, respectively. In fiber optical plug 9, foil 13 acts as a polarizer. In fiber optical plug 10, foil 14 acts as an analyzer. The transmitting directions (the directions of polarization of light passing through the polarizer or analyzer) of the polarizer and the analyzer are parallel to one another and form an angle of 45° with the longitudinal axis of the sensor element 4.

The entire optical movement sensor is made from nonmetallic materials. Thus, the belt 3 may be made of leather, the two buckle parts 1 and 2, the cotter pins 5 and 6, and the fiber optical plug of plastic, and the sensor element 4 of glass or transparent plastic.

Figure 2:
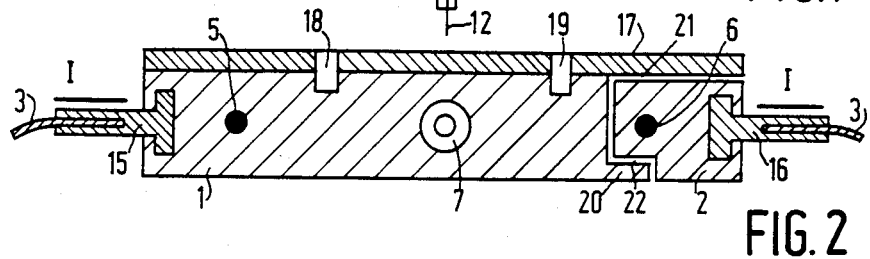
FIG. 2 is a cross-section view of the buckle along the line II—II in FIG. 1.

FIG. 2 is a sectional view along the line II—II in FIG. 1. The two ends of the belt 3 are connected to T-shaped fixing devices 15 and 16. As FIG. 1 also shows, devices 15 and 16 can be slid into the two buckle parts 1 and 2.

FIG. 2 shows the two cotter pins 5 and 6 and socket 7 in section. FIG. 2 also indicates that the front side of the buckle is covered by a plate 17 which is fixed to buckle part 1 by plastic screws 18 and 19. The plate 17 and a projection 20 of buckle part 1 form a guide for buckle part 2 which is thereby secured against lateral deviations by silicone washers 21 and 22. The elastic silicone washers 21 and 22 also prevent static and sliding friction losses due to the relative movements of the two buckle parts 1 and 2.

Figure 3:
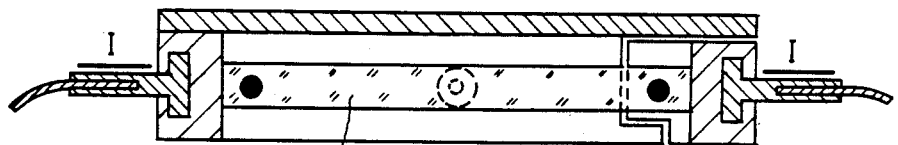
FIG. 3 is a cross-sectional view of the buckle along the line III—III in FIG. 1.

FIG. 3 is a sectional view of the buckle along the line III—III in FIG. 1. In FIG. 3, a possible configuration of the sensor element 4 is illustrated. Both the width and thickness of the plate-shaped sensor element 4 depend in this case on the required sensitivity of the optical movement sensor. The choice of material also affects the deformability and, therefore, the sensitivity of the sensor element 4. A movement sensor with a sensor element 4 of light-transmitting plastic has a greater sensitivity than a movement sensor with a sensor element 4 made of glass because plastic deforms more readily than glass.

Figure 4:
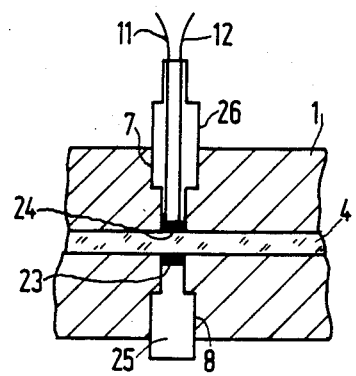
FIG. 4 is a cross-sectional view of a part of the buckle in which the transmitting and receiving light guides are housed in a fiber optical plug.

FIG. 4 is a sectional view of a part of the buckle in which the transmitting and receiving light guides 11 and 12 are arranged on one side of the sensor element 4. The transmitting and receiving light guides 11 and 12 are connected in this case to buckle part 1 by a single fiber optical plug 26. Mounted on the opposite side of the sensor element 4 to the ends of transmitting and receiving light guides 11 amd 12 is a mirror 23.

Mirror 23 may be, for example, a dielectric laminated mirror which comprises several thin, transparent $\lambda/4$ layers of alternatingly high and low refractive index. Such mirrors can have a reflectivity of approximately 99.9%.

Between the ends of transmitting and receiving light guides 11 and 12 the fiber optical plug 26 has a polarization foil 24. Foil 24 functions as a polarizer for the light emitted from the transmitting light guide and an an analyzer for the light coupled from the mirror 23 to the receiving light guide 12. The transmitting direction (the direction of polarization of light passing through the polarizer) of the polarization foil 24 forms an angle of 45° with respect to the longitudinal axis of the sensor element 4.

The mirror can be mounted at the bottom of a dummy plug 25 which has the same cross-section as a fiber optical plug and which therefore can be inserted in socket 8. The stress on the belt placed around the upper body or stomach of the patient is altered by every deformation caused by heart and respiratory activity but also by intestinal, swallowing and muscle movements such that the tensile stress acting on the sensor element 4 is also changed thereby. The elliptical polarization of the light emitted from transmitting light guide 11 and plane-polarized by polarizer 13 or 24 increases as the tensile stress acting on the sensor element 4 increases. After passing through sensor element 4, plane-polarized light is filtered from the elliptically polarized light by analyzer 14. The intensity of this plane polarized light when polarizer 13 and analyzer 14 have parallel transmitting directions decreases as the ellipticity of the light in sensor element 4 increases (i.e. the greater the tensile stress transmitted from the belt to the sensing element 4). The intensity of the light coupled to the receiving light guide 12 provides information, therefore, on the tensile stress on the belt-shaped movement sensor and thus on variations in the girth of the human body being examined.

In the case of the embodiment illustrated in FIG. 4, the light emitted by the transmitting light guide 11 is plane-polarized by the polarization foil 24 acting initially as a polarizer. The light by sensor element 4 is elliptically polarized as a function of the tensile stress acting on the sensing element 4. This elliptically polarized light is reflected by the mirror 23 through the sensing element 4 which, in addition, elliptically polarizes the light in such a way that the small axis of the polarization ellipse is reduced and the large axis is increased. The light then passes through the same polarization foil 24, this time acting as an analyzer and is coupled to the receiving light guide 12.

During this process, the analyzer filters from the elliptically polarized light plane-polarized light. The intensity of the plane polarized light decreases very considerably with an increase in the tensile stress acting on the sensor element 4 such that even small deformations of the human body under examination can be detected by measurement of this intensity.

What is claimed is:

1. An optical movement sensor for detecting deformation of a human body, said sensor comprising:
    a belt for placement around the body, said belt having first and second ends;
    a buckle having a first part attached to the first end of the belt and a second part attached to the second end of the belt;
    a light transmitting sensor element connecting the first and second parts of the buckle to each other;
    a transmitting light guide having an end arranged in the first part of the buckle to illuminate the sensor element;
    a receiving light guide having an end arranged in the first part of the buckle to receive light from the transmitting light guide after the light passes through the sensing element;
    a polarizer arranged in the first part of the buckle between the end of the transmitting light guide and the sensor element; and
    an analyzer arranged in the first part of the buckle between the end of the receiving light guide and the sensor element.

2. An optical movement sensor as claimed in claim 1, characterized in that the receiving and transmitting light guides are arranged on opposite sides of the sensor element.

3. An optical movement sensor as claimed in claim 1, characterized in that:

the receiving and transmitting light guides are arranged on the same side of the sensor element; and
the sensor further comprises a mirror arranged in the first part of the buckle to receive light which passes through the sensor element from the transmitting light guide, and to reflect said light back through the sensor element to the receiving light guide.

4. An optical movement sensor as claimed in claim 3, characterized in that:
the sensor further comprises a plug, said plug containing the transmitting and receiving light guides and a polarization foil arranged in front of the ends of the light guides; and
the first part of the buckle contains a socket for the plug.

5. An optical movement sensor for detecting deformation of a human body during nuclear spin tomography, said sensor comprising:
a belt for placement around the body, said belt having first and second ends;
a buckle having a first part attached to the first end of the belt and a second part attached to the secone end of the belt;
a light transmitting sensor element connecting the first and second parts of the buckle to each other;
a transmitting light guide having an end arranged in the first part of the buckle to illuminate the sensor element;
a receiving light guide having an end arranged in the first part of the buckle to receive light from the transmitting light guide after the light passes through the sensing element;
a polarizer arranged in the first part of the buckle between the end of the transmitting light guide and the sensor element; and
an analyzer arranged in the first part of the buckle between the end of the receiving light guide and the sensor element;
characterized in that the optical movement sensor is entirely made of nonmetallic materials.

6. An optical movement sensor as claimed in claim 5, characterized in that the receiving and transmitting light guides are arranged on opposite sides of the sensor element.

7. An optical movement sensor as claimed in claim 5, characterized in that:
the receiving and transmitting light guides are arranged on the same side of the sensor element; and
the sensor further comprises a mirror arranged in the first part of the buckle to receive light which passes through the sensor element from the transmitting light guide, and to reflect said light back through the sensor element to the receiving light guide.

8. An optical movement sensor as claimed in claim 7, characterized in that:
the sensor further comprises a plug, said plug containing the transmitting and receiving light guides and a polarization foil arranged in front of the ends of the light guides; and
the first part of the buckle contains a socket for the plug.

* * * * *